(12) United States Patent
Gomaa et al.

(10) Patent No.: US 8,075,629 B2
(45) Date of Patent: Dec. 13, 2011

(54) ORTHOPAEDIC PROSTHESIS HAVING A SEATING INDICATOR

(75) Inventors: Said T. Gomaa, Fort Wayne, IN (US); Jason T. Sherman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 278 days.

(21) Appl. No.: 12/338,510

(22) Filed: Dec. 18, 2008

(65) Prior Publication Data

US 2010/0161070 A1 Jun. 24, 2010

(51) Int. Cl.
*A61F 2/32* (2006.01)
(52) U.S. Cl. .................................................... 623/22.21
(58) Field of Classification Search .... 623/22.11–22.39, 623/23.16, 23.49, 18.12; 606/91
See application file for complete search history.

(56) References Cited

U.S. PATENT DOCUMENTS

| | | | | |
|---|---|---|---|---|
| 3,745,995 A * | 7/1973 | Kraus | ................................ | 602/2 |
| 5,141,512 A | 8/1992 | Farmer et al. | | |
| 5,318,571 A | 6/1994 | Benson | | |
| 5,702,476 A * | 12/1997 | Limacher et al. | .......... | 623/22.28 |
| 5,755,794 A | 5/1998 | Benson | | |
| 5,824,078 A | 10/1998 | Nelson et al. | | |
| 5,981,828 A | 11/1999 | Nelson et al. | | |
| 6,293,971 B1 | 9/2001 | Nelson et al. | | |
| 6,302,890 B1 | 10/2001 | Leone, Jr. | | |
| 6,623,488 B1 | 9/2003 | Leone, Jr. | | |
| 2004/0172502 A1 * | 9/2004 | Lionetta et al. | ................ | 711/112 |
| 2006/0190011 A1 | 8/2006 | Ries | | |
| 2007/0179739 A1 | 8/2007 | Donofrio et al. | | |
| 2008/0306486 A1 | 12/2008 | Lye | | |

FOREIGN PATENT DOCUMENTS

| | | |
|---|---|---|
| CA | 2 148 657 A1 | 11/1996 |
| CA | 2 250 446 | 6/1999 |
| EP | 0 327 509 B1 | 8/1989 |
| EP | 0353171 | 1/1990 |
| EP | 0 807 426 A2 | 11/1997 |
| EP | 1 835 967 A1 | 9/2007 |
| FR | 2649005 | 1/1991 |
| IE | 880739 | 3/1990 |

(Continued)

OTHER PUBLICATIONS

European Search Report for European Patent Application No. 09178127.8-2310, Apr. 22, 2010, 5 pgs.

*Primary Examiner* — Thomas J Sweet
*Assistant Examiner* — Jason-Dennis Stewart
(74) *Attorney, Agent, or Firm* — Barnes & Thornburg LLP (57) ABSTRACT

An orthopaedic prosthesis includes a curved outer surface configured to abut a patient's bone when the orthopaedic prosthesis is implanted therein. The outer surface may or may not be electrically conductive. A channel is defined in the outer surface and extends from a rim of the outer surface to a location on the outer surface. One or more electrical conductors is positioned in the channel and extends outwardly from the channel at the rim of the outer surface. A switch is positioned at the first location and is configured to establish an electrical connection between the electrical conductor and the outer surface and/or another electrical conductor when the first location of the outer surface contacts the patient's bone. The switch may be embodied as an end of the electrical conductor or a more complex switch such as a push-button type switch.

20 Claims, 6 Drawing Sheets

FOREIGN PATENT DOCUMENTS

| | | |
|---|---|---|
| JP | 63318939 A | 12/1988 |
| JP | 2000325374 A | 11/2000 |
| NZ | 548764 A | 12/2007 |
| WO | 2006/060632 A1 | 6/2006 |
| WO | 2006/109983 A1 | 10/2006 |
| WO | 2007/056810 A1 | 5/2007 |
| WO | 2008089723 | 7/2008 |

* cited by examiner

ORTHOPAEDIC PROSTHESIS HAVING A SEATING INDICATOR

TECHNICAL FIELD

The present disclosure relates generally to orthopaedic prostheses and particularly to orthopaedic prostheses having an indicator coupled thereto for providing an indication when the prostheses is properly seated.

BACKGROUND

Orthopaedic prostheses are implanted in patients by orthopaedic surgeons to, for example, correct or otherwise alleviate bone and/or soft tissue loss, trauma damage, and/or deformation of the bone(s) of the patients. Orthopaedic prostheses replace a portion of or the complete joint of a patient. For example, the orthopaedic prosthesis may replace the patient's hip, shoulder, ankle, knee or other joint. In the case of a hip replacement, the orthopaedic prosthesis includes an acetabular cup, which is secured to the surgically-prepared acetabulum of the patient. The acetabular cup replaces the natural bearing surface of the acetabulum with a new bearing surface for the natural or prosthetic head of the patient's femur.

During the orthopaedic surgical procedure, a surgeon initially prepares the patient's bone to receive the orthopaedic prosthesis. For example, in the case of a hip orthopaedic surgical procedure, the surgeon may initially ream the patient's acetabulum. The orthopaedic prosthesis is subsequently coupled to the patient's surgically-prepared bone. Depending on the particular orthopaedic surgical procedure, the type of orthopaedic prosthesis, and/or other factors, it may be difficult for the surgeon to determine when the orthopaedic prosthesis is fully seated into the patient's bone. For example, it may be difficult for the orthopaedic surgeon to visually confirm when particular portions of the orthopaedic prosthesis have contacted the patient's bone.

SUMMARY

According to one aspect, an acetabular cup includes an electrically conductive outer surface, a first electrical conductor, and a first switch. The electrically conductive outer surface may be configured to confront a portion of a patient's acetabulum when the acetabular cup is implanted in the patient. The outer surface may include a first channel defined therein that extends from a rim of the outer surface to a first location of the outer surface. The first electrical conductor may be positioned in the first channel. The first electrical conductor may include a first end that extends out of the first channel at the rim of the outer surface. The first switch may be located at the first location of the outer surface. The first switch may have a first state wherein an electrical connection between the first electrical conductor and the outer surface is broken and a second state wherein an electrical connection between the first electrical conductor and the outer surface is established. The first switch may be configured such that the first switch is positioned in the second state when the first location of the outer surface contacts the patient's acetabulum.

In some embodiments, the first switch may be embodied as a second end of the first electrical conductor. In such embodiments, the second end of the first electrical conductor may extend out of the first channel at the first location of the electrically conductive outer surface and may be positionable such that the second end comes into contact with the electrically conductive outer surface when the first location of the outer surface contacts the patient's acetabulum.

In other embodiments, the first switch may be embodied as a push-button switch. In such embodiments, the push-button switch may be biased to the first state. Additionally, the push-button switch may be configured such that the push-button switch is positioned in the second state when the first location of the outer surface contacts the patient's acetabulum. Additionally, in some embodiments, the electrically conductive outer surface may include a recessed area at the first location. In such embodiments, the push-button switch may be positioned in the recessed area.

In some embodiments, the electrically conductive outer surface may include a second channel defined therein. The second channel may extend from the rim of the outer surface to a second location of the outer surface. Additionally, in such embodiments, the acetabular cup may include a second electrical conductor and a second switch. The second electrical conductor may be positioned in the second channel. Additionally, the second electrical conductor may have a first end that extends out of the second channel at the rim of the outer surface. The second switch may be located at the second location of the outer surface.

Similar to the first switch, the second switch may have a first state wherein an electrical connection between the second electrical conductor and the outer surface is broken and a second state wherein an electrical connection between the second electrical conductor and the outer surface is established. The second switch may also be configured such that the second switch is positioned in the second state when the second location of the outer surface contacts the patient's acetabulum. Additionally, the second switch may be embodied as a second end of the second electrical conductor. In such embodiments, the second end of the second electrical conductor may extend out of the second channel at the second location of the electrically conductive outer surface and positionable such that the second end of the second electrical conductor comes into contact with the electrically conductive outer surface when the second location of the outer surface contacts the patient's acetabulum.

In some embodiments, the electrically conductive outer surface may include a first recessed area at the first location, a second recessed area at a second location of the outer surface, and a second channel defined in the outer surface. The second channel may extend from the first recessed area to the second recessed area. The first switch may be positioned in the first recessed area. In such embodiments, the acetabular cup may also include a second switch positioned in the second recessed area and a second electrical conductor positioned in the second channel. The second electrical conductor is electrically coupled to the first switch and the second switch. Additionally, the acetabular cup may include a third electrical conductor electrically coupled to the second switch. In such embodiments, a portion of the third electrical conductor may be positioned in the first channel. The third electrical conductor may have a first end that extends out of the first channel at the rim of the outer surface.

Additionally, in some embodiments, the first and second switches may be embodied as first and second push-button switches. In such embodiments, each of the first and second push-button switches may be biased to the first state. The first switch may be configured such that the first push-button switch is positioned in the second state when the first location of the outer surface contacts the patient's acetabulum and the second switch may be configured such that the second push-button switch is positioned in the second state when the second location of the outer surface contacts the patient's acetabulum According to one aspect, an orthopaedic prosthesis may include a curved outer surface and an electrical conductor. The curved outer surface may be electrically conductive and may be configured to confront a portion of a patient's bone when the orthopaedic prosthesis is implanted in the patient's bone. The curved outer surface may include a channel defined therein. The channel may extend from a rim of the curved outer surface to a first location of the curved outer surface. The electrical conductor may be positioned in the channel. The electrical conductor may have a first end that extends out of the channel at the rim of the curved outer surface and a second end that extends out of the channel at the first location of the curved outer surface. The second end of the electrical conductor may be positionable in a first position apart from the curved outer surface and a second position in contact with the curved outer surface.

In some embodiments, the second end of the electrical conductor may be positioned such that the second end is moved to the second position when the first location of the curved outer surface contacts the patient's bone. Additionally, in some embodiments, the electrical conductor may include a non-conductive polymer cladding and a conductive polymer wire core located within the non-conductive polymer cladding. In such embodiments, the conductive polymer wire core extends outwardly from the non-conductive polymer at the second end of the electrical conductor.

According to yet another aspect, an acetabular cup may include an outer surface configured to confront a portion of a patient's acetabulum when the acetabular cup is implanted in the patient. The outer surface may include a channel defined therein that extends from a rim of the outer surface to a first location of the outer surface. The acetabular cup may also include switch located at the first location of the outer surface. Additionally, the acetabular cup may include a first electrical conductor and a second electrical conductor. The first electrical conductor may be positioned in the channel and may include a first end that extends out of the channel at the rim of the outer surface and a second end electrically coupled to the switch. The second electrical conductor may also be positioned in the channel and may include a first end that extends out of the channel at the rim of the outer surface and a second end electrically coupled to the switch. The switch may have a first state wherein an electrical connection between the first electrical conductor and the second electrical conductor is broken and a second state wherein an electrical connection between the first electrical conductor and the second electrical conductor is established.

According to a further aspect, a method for implanting an orthopaedic prosthesis in a bone of a patient may include contacting the patient's bone with the orthopaedic prosthesis, measuring the resistance between an outer surface of the orthopaedic prosthesis and an electrical conductor coupled to the orthopaedic prosthesis while the orthopaedic prosthesis is in contact with the patient's bone, and adjusting the positioning of the orthopaedic prosthesis if the measured resistance is greater than a predetermined threshold. The predetermined resistance threshold includes a first resistance value indicative of the resistance of the outer surface of the orthopaedic prosthesis and a second resistance value indicative of the resistance of the electrical conductor.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 1:
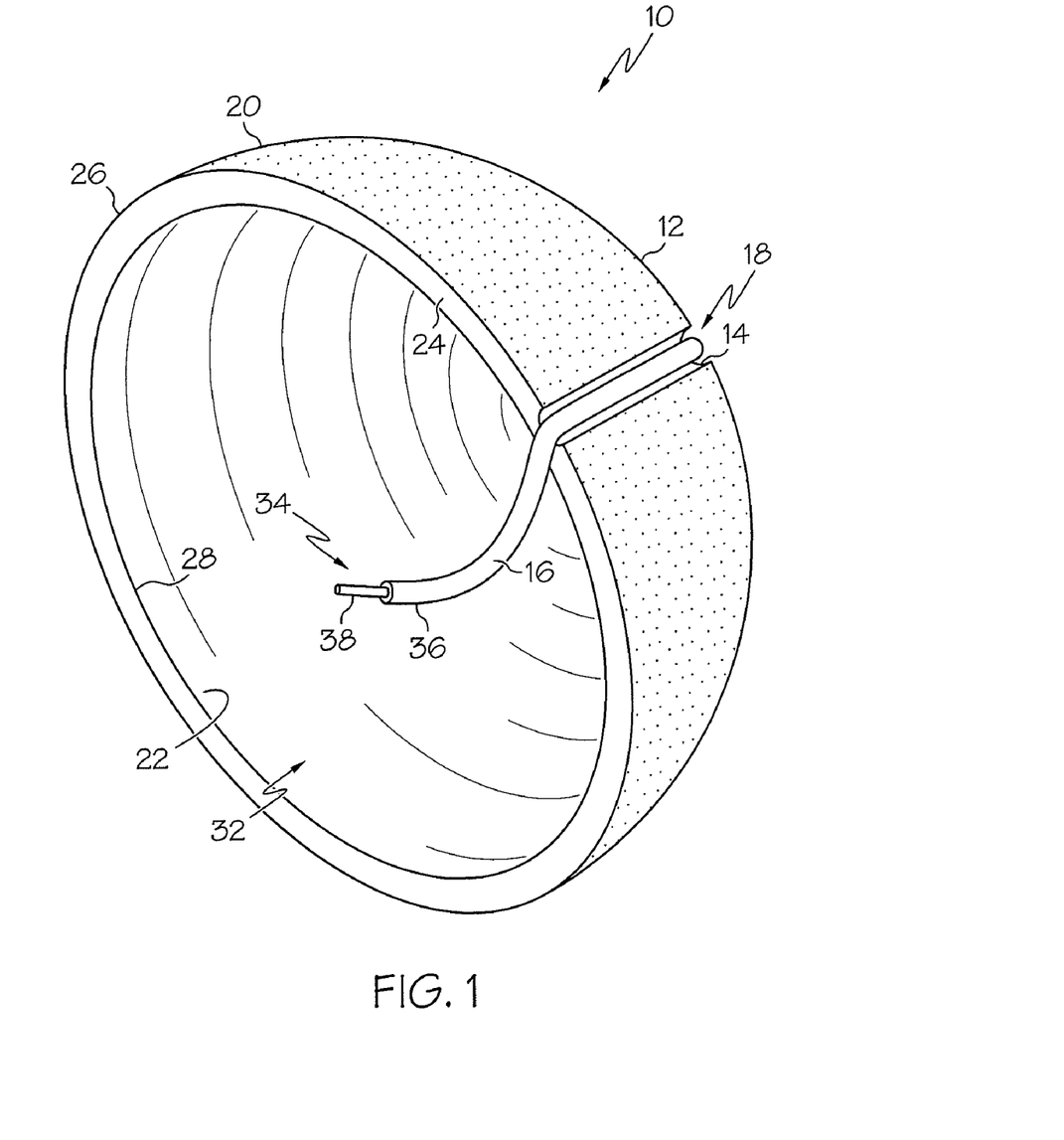
FIG. 1 is a perspective view of one embodiment of an orthopaedic prosthesis having a seating indicator coupled thereto.

Referring to FIG. 1, in one embodiment, an orthopaedic prosthesis 10 includes a curved outer surface 12 having a channel 14 defined therein, an electrical conductor 16 positioned in the channel 14, and a switch 18 positioned at a location of the curved outer surface 12 and electrically coupled to the electrical conductor 16. In the illustrative embodiment, the orthopaedic prosthesis 10 is embodied as an acetabular cup 20, but may be embodied as other prostheses in other embodiments. For example, the orthopaedic prosthesis 10 may be embodied as any orthopaedic prosthesis having a curved outer surface, such as a shoulder or ankle prosthesis, which can present difficulties for an orthopaedic surgeon to determine whether the prosthesis is properly seated into the patient's bone (e.g., when particular portions of the prosthesis 10 contact the patient's bone) due to visual limitations. Accordingly, although the orthopaedic prosthesis 10 is discussed in detail below in regard to an acetabular cup 20, it should be appreciated that such features and description may be equally applicable to other orthopaedic prostheses including shoulder and ankle prostheses.

The acetabular cup 20 includes the curved outer surface 12, a curved inner surface 22, and a rim surface 24 extending from the edge or rim 26 of the curved outer surface 12 to the edge or rim 28 of the curved inner surface 22. The acetabular cup 20 may be formed from any suitable material capable of being secured to the acetabulum of a patient and supporting a natural or artificial head portion of the patient's femur. For example, the acetabular cup 20 may be formed from a ceramic material, a polymer material, a titanium alloy, or other implantable metal material. The illustrative acetabular cup 20 is a monoblock prosthesis formed of a single piece and configured to be implanted into the patient's acetabulum without the use of bone cement. As such, the illustrative acetabular cup 20 does not include mounting holes defined through the inner and outer surfaces 12, 22, respectively. However, in some embodiments, the acetabular cup 20 may include any number of mounting holes, which are commonly used with bone screws to secure the cup 20 to the patient's bone.

In other embodiments, the acetabular cup 20 may be formed from a number of separate parts. For example, in some embodiments, the acetabular cup 20 may include a bearing 30 (see FIG. 2) configured to be received in a cavity 32 defined by the inner curved surface 22. In such embodiments, the bearing provides an artificial surface on which the natural or artificial head portion of the femur of the patient may articulate. The bearing may be formed from any material suitable for such purpose. For example, the bearing may be formed from a metallic material, a ceramic material, a polymeric material such as polyethylene or ultra-high molecular weight polypropylene (UHMWPE), and/or the like.

In the illustrative embodiment, the curved outer surface 12 is electrically conductive. For example, in some embodiments, the curved outer surface 12 may have an electrical conductivity of 5 siemens per meter or greater. In embodiments wherein acetabular cup 20 is formed from a non-electrically conductive material, such as a ceramic or polymer material, the acetabular cup 20 may include an electrically conductive coating or texture applied to the outer surface 12 so as to form the electrically conductive outer surface 12. In some embodiments, the conductive coating may be configured to also enhance bone growth. Additionally, even in embodiments wherein the acetabular cup 20 is formed from an electrically conductive material, such as a metallic material, the electrically conductive coating may also be applied to the outer surface of the cup 20.

Figure 2:
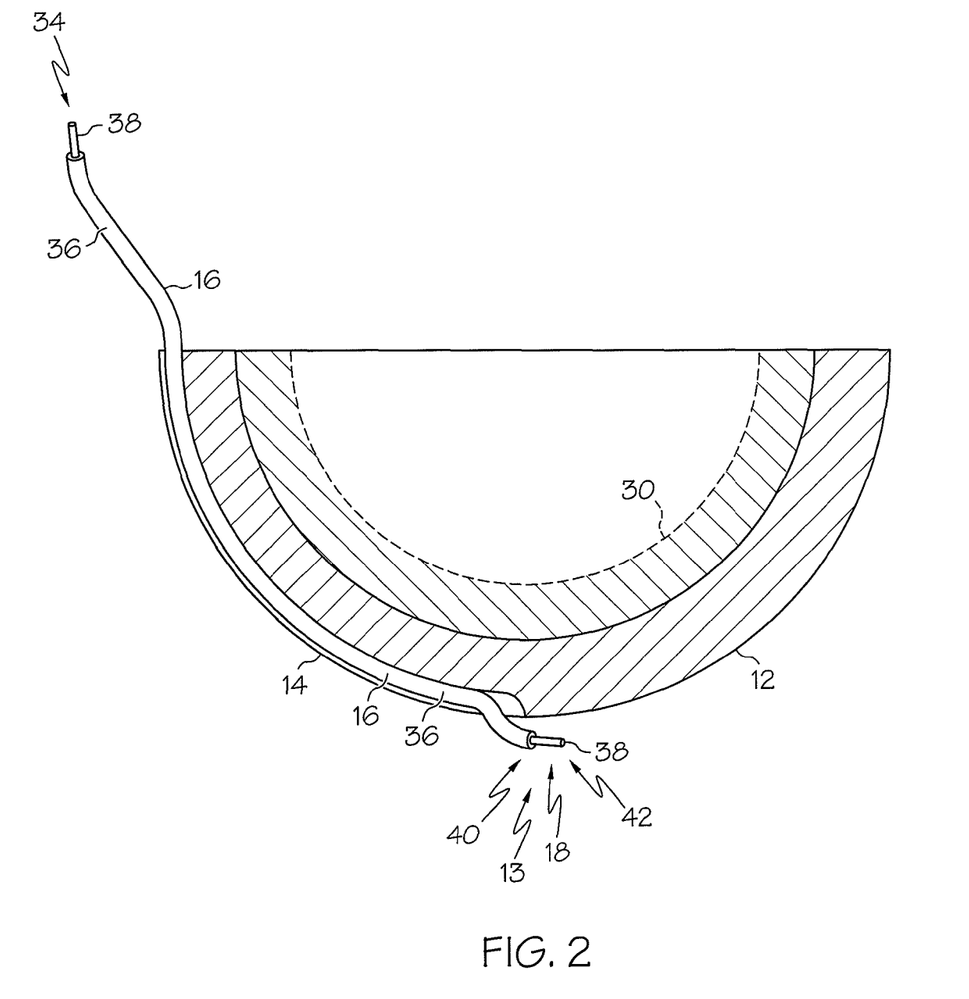
FIG. 2 is a cross-sectional view of the orthopaedic prosthesis of FIG. 1.
Figure 3:
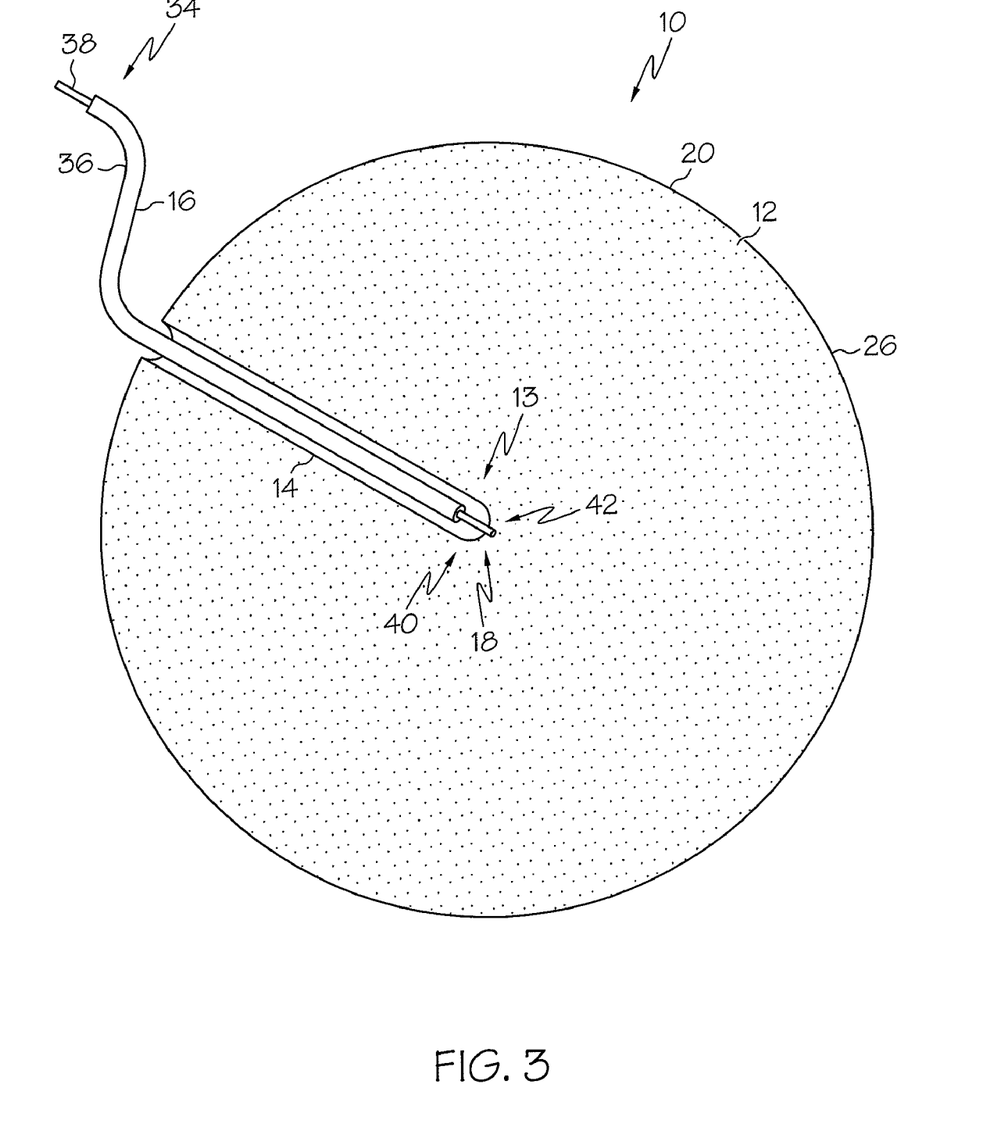
FIG. 3 is a plan view of the outer surface of the orthopaedic prosthesis of FIG. 1.
Figure 4:
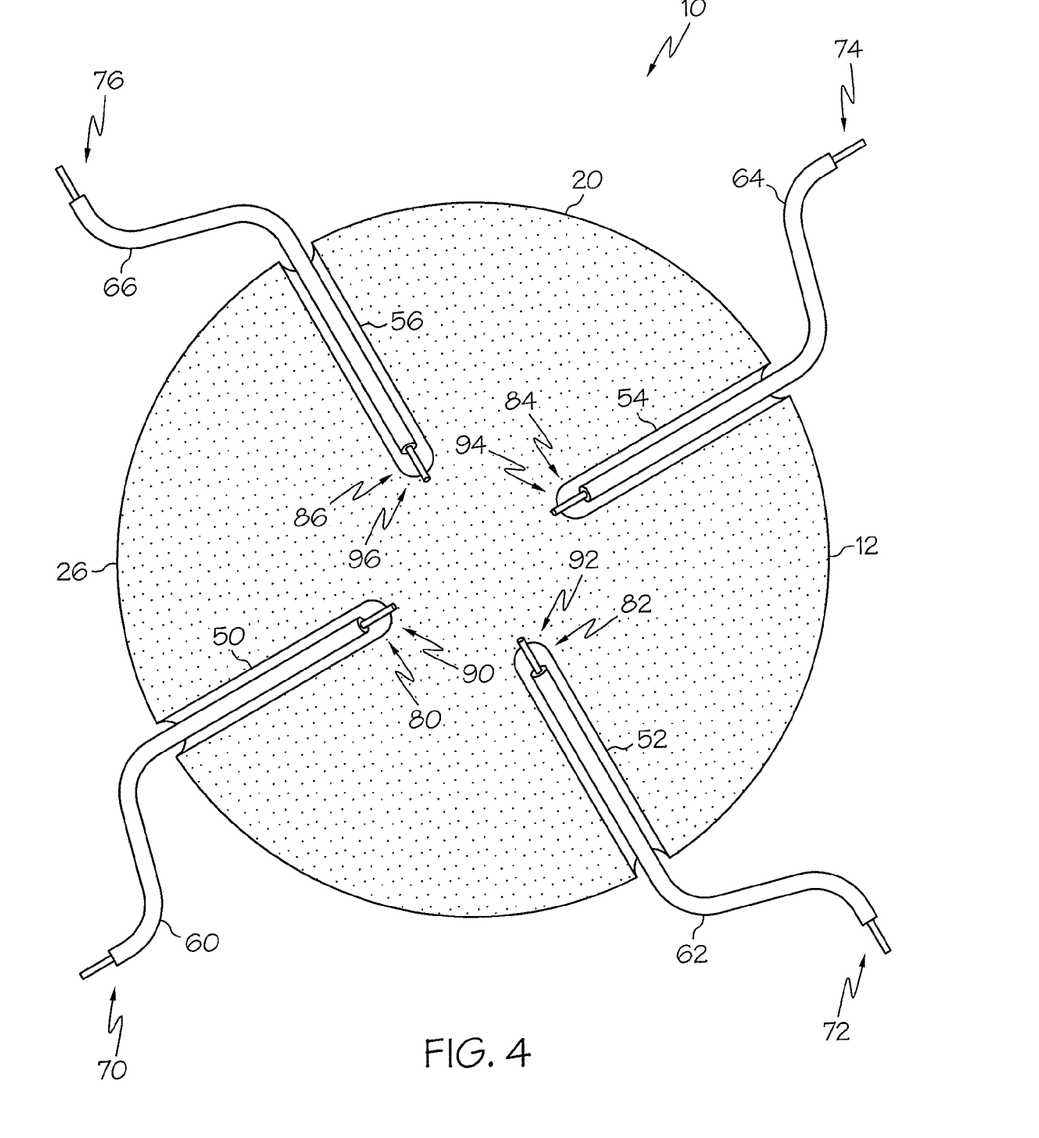
FIG. 4 is a plan view of the outer surface of another embodiment of the orthopaedic prosthesis of FIG. 1.

As discussed above, the outer surface 12 of the acetabular cup 20 includes the channel 14 defined therein. The channel 14 extends from the rim 26 of the outer surface 12 to a predetermined location 13 of the outer surface 12. The location 13 to which the channel 14 extends may be any location of interest on the outer surface 12 that contacts the patient's bone when the acetabular cup 20 is properly seated therein. For example, as illustrated in FIGS. 2 and 3, in some embodiments, the channel 14 may extend from the rim 26 to a location of the outer surface 12 substantially corresponding to the apex of the dome-shaped outer surface 12.

The electrical conductor 16 is positioned in the channel 14 and includes a first end 34 that extends out of the channel 14 at the rim 26 of the outer surface 12. In the illustrative embodiment, the electrical conductor 16 extends out of the channel 14 a length sufficient enough such that the electrical conductor 16 may be grasped by an orthopaedic surgeon while the acetabular cup 20 is fully seated into the patient's bone.

In the illustrative embodiment, the electrical conductor 16 is embodied as a wire, but may be embodied as other types of electrical conductors in other embodiments such as an electrical trace, rod, or other electrically conductive path. The electrical conductor 16 illustratively includes a non-electrically conductive cladding 36 and an electrically conductive inner core 38, which is surrounded by the cladding 36. In one particular embodiment, the cladding 36 is formed from a non-electrically conductive polymer cladding and the electrically conductive inner core 38 is formed from an electrically conductive polymer. However, the electrical conductor 16 may be formed from other bio-compatible materials in other embodiments. The cladding 36 provides an amount of electrical isolation to the inner core 38. To access the inner core 38, the cladding 36 may be stripped back or otherwise removed such that the inner core 38 extends therefrom as illustrated at the first end 34 of the electrical conductor 16 in FIG. 1.

The electrical conductor 16 may be held in place in the channel 14 via friction or via use of an adhesive. For example, in some embodiments, the channel 14 may have a width slightly larger than the outer width of the cladding 36 such that the electrical conductor 16 may be pressed into the channel 14 and held in place via frictional forces. Alternatively, a bio-compatible adhesive may be used to secure the electrical conductor 16 in the channel 14. In some embodiments, the adhesive may be semi-permanent such that the electrical conductor 16 may be removed from the channel 14 via application of an appropriate amount of force as discussed below in regard to FIG. 8.

As shown in FIG. 2, the switch 18 is positioned at the predetermined location 13 of the curved outer surface 12 (i.e., the location of interest that contacts the patient's bone when the cup 20 is properly seated). In the illustrative embodiment, the switch 18 is positioned near the apex of the dome-shaped outer surface 12. The switch 18 may be a simple switch or a complex switch. For example, in the illustrative embodiment, the switch 18 is embodied as a second end 40 of the electrical conductor 16. However, in other embodiments as discussed in more detail below in regard to FIGS. 5 and 6, the switch 18 may be embodied as a more complex switch that is electrically coupled to electrical conductor 16.

The illustrative switch 18 illustrated in FIGS. 1-4 is formed from the second end 40 of the electrical conductor 16 by removal of the non-conductive cladding 36, which exposes an end 42 of the inner core 38. The end 42 of the inner core 38 is positioned to extend out of the channel 14 and over a portion of the electrically conductive outer surface 12 without contacting the surface 12. However, when the acetabular cup 20 is properly seated in the patient's acetabulum, the end 42 of the inner core 38 is pressed against the electrically conductive outer surface 12 by the patient's bone thereby establishing a connection between the electrical conductor 16 and the outer surface 12.

As such, the switch 18 includes two states, a non-conductive state and a conductive state. In the first state, the end 42 of the inner core 38 is spaced apart from the electrically conductive outer surface 12 and no electrical connection is established between the electrical conductor 16 and the outer surface 12. The switch 18 is positioned in the first state prior to implantation of the acetabular cup 20. In the second state, the end 42 of the inner core 38 is in contact with the electrically conductive outer surface 12 and an electrical connection is established between the electrical conductor 16 and the outer surface 12. As such, as discussed in more detail below, an orthopaedic surgeon may determine whether the acetabular cup 20 is properly seated (i.e., whether the predetermined location 13 of the outer surface 12 is in contact with the patient's bone) by measuring the resistance between the outer surface 12 of the acetabular cup 20 and the first end 34 of the electrical conductor. A measured resistance value less than a predetermined threshold value is indicative of proper seating of the acetabular cup 20 because the outer surface 12 is in contact with the patient's bone causing the switch 18 to be positioned in the second, conductive state.

Although the embodiment illustrated in FIGS. 1-3 includes a single switch 18, the acetabular cup 20 may include any number of switches in other embodiments. Each switch may be used to detect whether a corresponding location of the outer surface 12 is in contact with the patient's bone to thereby determine proper seating of the cup 20. For example, in the embodiment illustrated in FIG. 4, the acetabular cup 20 includes four channels 50, 52, 54, 56, each similar to the channel 14, defined in the electrically conductive outer surface 12. An electrical conductor 60, 62, 64, 66, each similar to the electrical conductor 16, is positioned in each respective channel 50, 52, 54, 56. Each electrical conductor includes a first end 70, 72, 74, 76 extending from the respective channel 50, 52, 54, 56 at the rim 26 of the outer surface 12. Additionally, each electrical conductor 60, 62, 64, 66 includes a second end 80, 82, 84, 86, each of which forms a respective switch 90, 92, 94, 96 in the manner described above in regard to switch 18. Although the channels 50, 52, 54, 56 are defined in the outer surface 12 in a symmetrical pattern in the embodiment illustrated in FIG. 4, it should be appreciated that the channels 50, 52, 54, 56 may be defined in any orientation relative to each other in other embodiments such that a corresponding switch 18, 90, 92, 94, 96 may be defined at any location of the outer surface 12.

Figure 5:
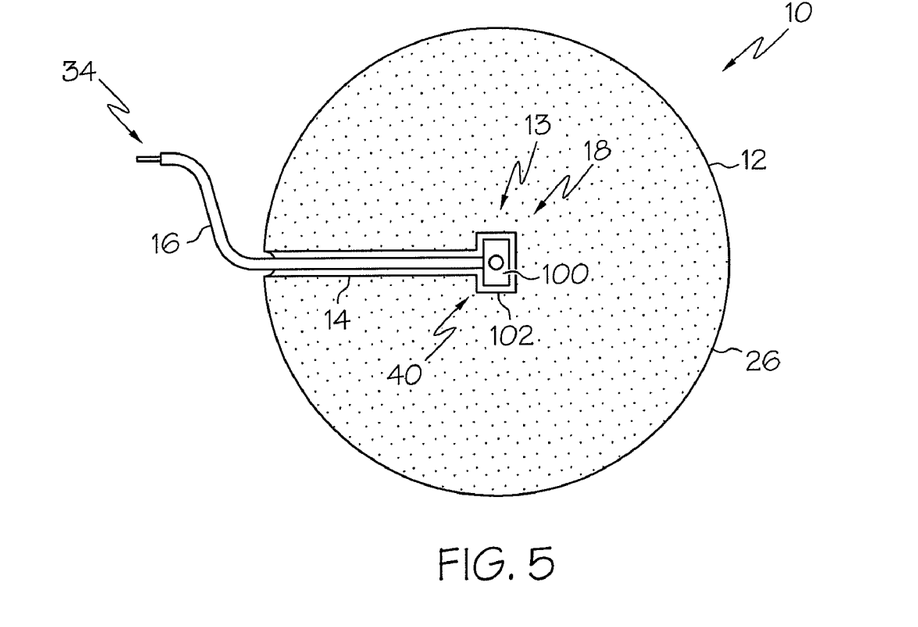
FIG. 5 is a plan view of the outer surface of another embodiment of the orthopaedic prosthesis of FIG. 1.
Figure 6:
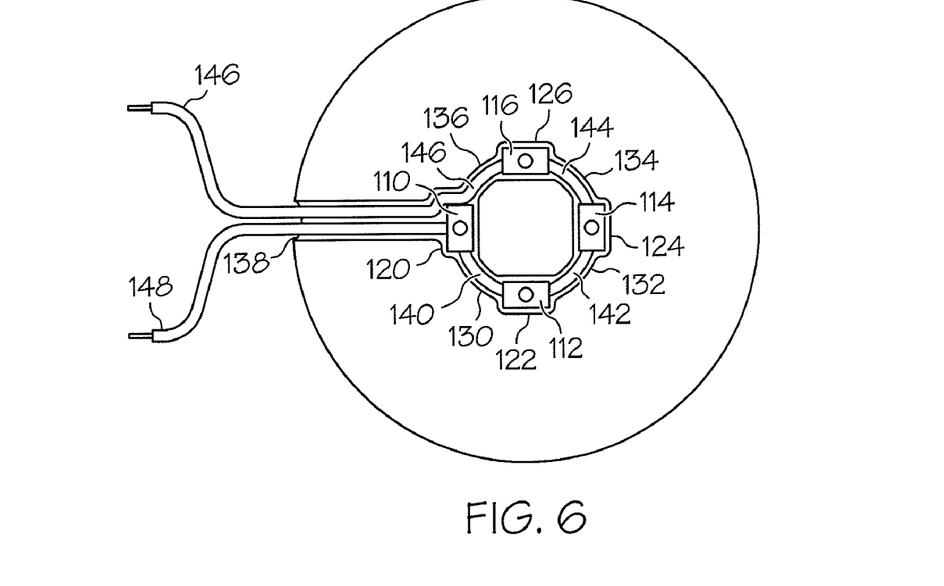
FIG. 6 is a plan view of the outer surface of another embodiment of the orthopaedic prosthesis of FIG. 1.

In some embodiments, the switch 18 may be embodied as a complex switch. For example, in some embodiments, as illustrated in FIGS. 5 and 6, the switch 18 may be embodied as a push-button switch 100. The push-button switch 100 may be embodied as any type of push-button switch. For example, the push-button switch 100 may be a plunger-type switch having a plunger configured to be depressed when the switch contacts the patient's bone. Alternatively, the push-button switch 100 may be a dome-type switch having a dome or ceiling configured to be collapsed when the switch contacts the patient's bone. Regardless, the push-button switch 100 is positioned in a recessed area 102 defined in the outer surface 12 of the acetabular cup 20 at the predetermined location 13. The push-button switch 100 may be secured in the recessed area 102 using any suitable adhesive or connector. In such embodiments, the channel 14 extends from the rim 26 of the outer surface 12 to the recessed area 102.

The push-button switch 100 is electrically coupled to the electrical conductor 16 and to the electrically conductive outer surface 12. As discussed above in regard to the switch 18, the push-button switch 100 includes two states, a non-conductive state and a conductive state. In the first state, no electrical connection is established between the electrical conductor 16 and the outer surface 12. In the second state, the switch 100 is activated (e.g., the switch 100 contacts a portion of the patient's bone) and an electrical connection is established between the electrical conductor 16 and the outer surface 12.

As discussed above, the acetabular cup 20 may include any number of switches 18, 100 to detect whether corresponding locations of the outer surface are in contact with the patient's bone. For example, as illustrated in FIG. 6, the acetabular cup 20 may include four push-button switches 110, 112, 114, 116 positioned in respective recessed areas 120, 122, 124, 126. In such embodiments, the outer surface 12 includes a number of channels 130, 132, 134, 136 connecting each of the recessed areas 120, 122, 124, 126. The channel 130 extends from the recessed area 120 to the recessed area 122. The channel 132 extends from the recessed area 122 to the recessed area 124. The channel 134 extends from the recessed area 124 to the recessed area 126. The channel 136 extends from the recessed area 126 to the recessed area 120. Additionally, a channel 138 extends from the rim 26 of the electrically conductive outer surface 12 to the recessed area 120. An electrical conductor 140 is positioned in the channel 138 and is electrically coupled to the push-button switch 110. An electrical conductor 142 is positioned in the channel 130 and is electrically coupled to the switches 110, 112. An electrical conductor 144 is positioned in the channel 131 and is electrically coupled to the switches 112, 114. An electrical conductor 144 is positioned in the channel 134 and is electrically coupled to the switches 114, 116. An electrical conductor 146 is positioned in the channel 136 and is electrically coupled to the switch 116. The electrical conductor 146 extends from the channel 136, through the channel 138, and extends out of the channel 138 at the rim 26 of the electrically conductive outer surface 12.

It should be appreciated that the embodiment of FIG. 6, includes two conductors 140, 146 extending out of the channel 138. In such embodiments, the switches 110, 112, 114, 116 are not electrically coupled to the outer surface 12. Additionally, the outer surface 12 may or may not be electrically conductive. For example, in the illustrative embodiment of FIG. 6, the outer surface 12 is not electrically conductive. In such embodiments, each of the switches 110, 112, 114, 116 either complete or break the electrical path defined by the electrical conductors 140, 142, 144, 146, 148. That is, each switch 110, 112, 114, 116 has a first state in which the electrical path defined by the electrical conductors 140, 142, 144, 146, 148 is broken and a second state in which the electrical path is completed. As such, as discussed in more detail below, an orthopaedic surgeon may determine whether the acetabular cup 20 is properly seated in such embodiments by measuring the continuity (or resistance) of the electrical path defined by the electrical conductors 140, 142, 144, 146, 148. Proper seating of the acetabular cup 20 is indicated when the electrical path is completed or broken depending on the type of switches 110, 112, 114, 116 used (i.e., the switches may be normally-open or normally-closed).

Although the acetabular cup 20 illustrated in FIG. 6 includes four separate switches 110, 112, 114, 116, the cup 20 may include a greater or smaller number of switches in other embodiments. For example, in some embodiments, the acetabular cup 20 may include a single switch similar to the embodiment illustrated in FIG. 5. However, because the single switch is not coupled to the outer surface 12 in such embodiments, an additional electrical conductor is included and extends out of the channel 14. Additionally, as discussed above in regard to FIG. 6, the outer surface 12 may not be electrically conductive in such embodiments. However, in other embodiments, the outer surface 12 may be electrically conductive and each switch 110, 112, 114, 116 may be electrically coupled to the electrically conductive outer surface 12. In such embodiments, the acetabular cup 20 includes a separate channel and electrical conductor for each switch similar to the embodiment illustrated in and described above in regard to FIG. 4.

Figure 7:
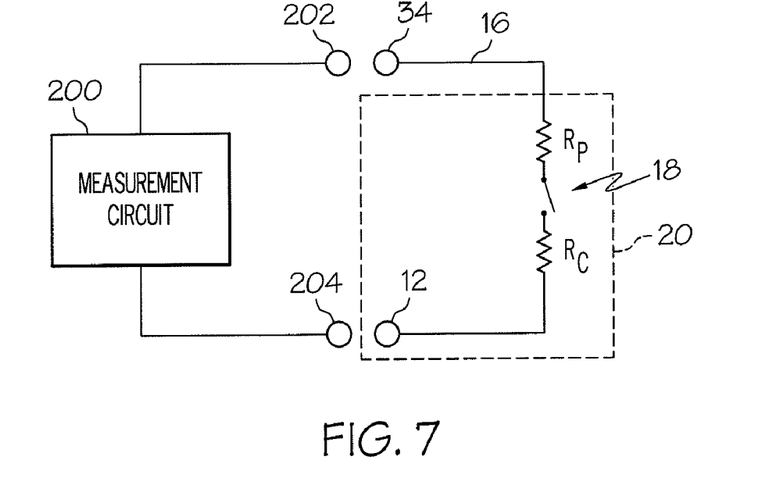
FIG. 7 is a simplified block diagram of one embodiment of a measuring circuit for use with the orthopaedic prosthesis of FIGS. 1-6.

Referring now to FIG. 7, an orthopaedic surgeon may determine whether the acetabular cup 12 is properly seated by measuring the resistance between the electrical conductor 16 (or conductors 70, 72, 74, 76 in the embodiment of FIG. 4) and the electrically conductive outer surface 12 of the cup (or between two conductors in the embodiment of FIG. 6). To do so, a measurement circuit 200 may be used. The measurement circuit 200 may be embodied as any type of circuit or device capable of measuring the resistance or impedance of a circuit. The measurement circuit 200 includes a first measurement probe 202, which is electrically coupled to the first end 34 of the electrical conductor 16. The measurement circuit 200 also includes a second measurement probe 204, which is electrically coupled to the electrically conductive outer surface 12 of the acetabular cup 20 (or the other electrical conductor in the embodiment of FIG. 6). The measurement circuit 200 measures the resistance between the these two points. A measured resistance below a predetermined threshold is indicative that the switch 18 has been positioned in the second state (i.e., the predetermined location 13 has contacted the patient's bone) and the acetabular cup 20 is properly positioned. As shown in FIG. 7, the predetermined resistance threshold includes or otherwise accounts for the resistance of the electrical conductor 16, Rp, and the resistance of the outer surface 12, Rc.

Figure 8:
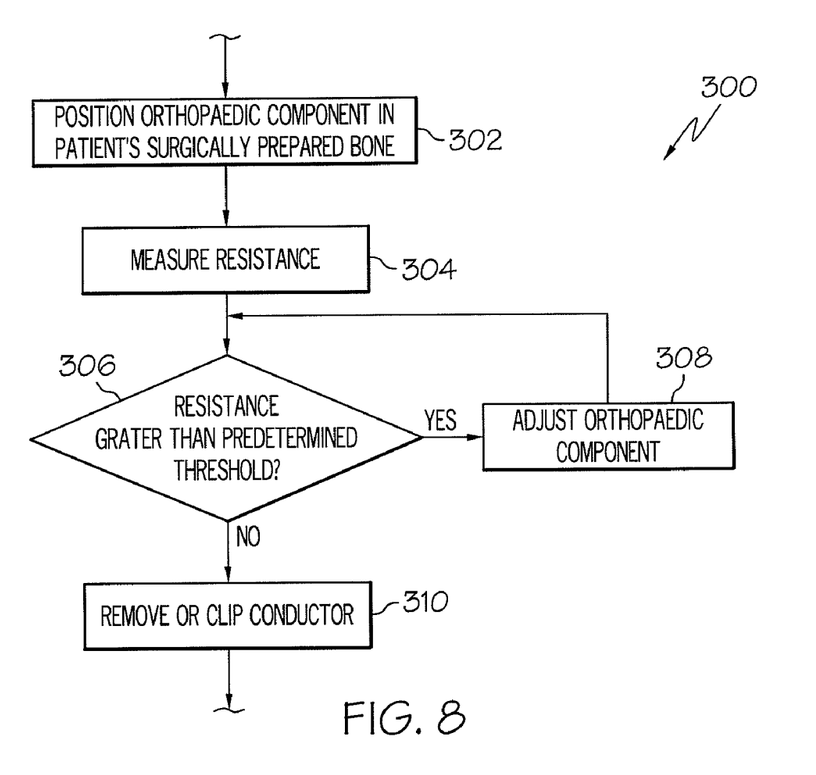
FIG. 8 is a simplified flowchart of a method for determining whether an orthopaedic prosthesis is seated.

Referring now to FIG. 8, a method 300 for determining whether the orthopaedic prosthesis 10 is properly seated begins with step 302. In step 302, the orthopaedic prosthesis 10 is positioned in the surgically-prepared bone of the patient. For example, in embodiments wherein the prosthesis 10 is embodied as the acetabular cup 20, the cup 20 is positioned in the patient's surgically-prepared acetabulum. After the prosthesis 10 has been so positioned, the orthopaedic surgeon measures the resistance between the electrical conductor 16 and the electrically conductive outer surface 12 of the acetabular cup 20 (or between the two electrical conductors in embodiments similar to the embodiment of FIG. 6) in step 304. In step 306, the measured resistance value is compared to the predetermined resistance threshold value. If the measured value is greater than the predetermined resistance threshold value, the position of the orthopaedic prosthesis 10 is adjusted in step 308. Additionally, in some embodiments, the bone of the patient may be re-shaped again in step 308. For example, in embodiments wherein the prosthesis 10 is embodied as an acetabular cup 20, the acetabulum of the patient may be re-reamed in step 308 to provide a better match to the acetabular cup 20. The resistance between the electrical conductor 16 and the outer surface 12 is again measured in step 306. If, however, the measured resistance is determined to be less than the predetermined resistance threshold in step 306, the orthopaedic prosthesis is considered to be properly seated. As such, the orthopaedic surgeon may trim or remove the electrical conductor 16. For example, in embodiments wherein the electrical conductor 16 is secured in the channel 14 via frictional forces, the orthopaedic surgeon may remove the electrical conductor 16 from the channel 14 by pulling on the end 34 of the electrical conductor 16.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the devices, systems, and methods described herein. It will be noted that alternative embodiments of the devices, systems, and methods of the present disclosure may not include all of the features described yet still benefit from at least some of the advantages of such features. Those of ordinary skill in the art may readily devise their own implementations of the devices, systems, and methods that incorporate one or more of the features of the present invention and fall within the spirit and scope of the present disclosure as defined by the appended claims.

The invention claimed is:

1. An acetabular cup comprising:
an electrically conductive dome-shaped outer surface configured to confront a portion of a patient's acetabulum when the acetabular cup is implanted in the patient, the dome-shaped outer surface including a first channel defined therein that extends from a rim of the dome-shaped outer surface to a first location of the dome-shaped outer surface, the first location positioned near an apex of the dome-shaped outer surface;
a first electrical conductor positioned in the first channel, the first electrical conductor having a first end that extends out of the first channel at the rim of the dome-shaped outer surface; and
a first switch located at the first location of the dome-shaped outer surface, the first switch having a first state wherein an electrical connection between the first electrical conductor and the dome-shaped outer surface is broken and a second state wherein an electrical connection between the first electrical conductor and the dome-shaped outer surface is established.

2. The acetabular cup of claim 1, wherein the first switch is configured such that the first switch is positioned in the second state when the first location of the dome-shaped outer surface contacts the patient's acetabulum.

3. The acetabular cup of claim 1, wherein the first switch comprises a second end of the first electrical conductor, the second end of the first electrical conductor extending out of the first channel at the first location of the electrically conductive dome-shaped outer surface and positionable such that the second end comes into contact with the electrically conductive dome-shaped outer surface when the first location of the dome-shaped outer surface contacts the patient's acetabulum.

4. The acetabular cup of claim 1, wherein the electrically conductive dome-shaped outer surface includes a second channel defined therein, the second channel extending from the rim of the dome-shaped outer surface to a second location of the dome-shaped outer surface, and further comprising:
a second electrical conductor positioned in the second channel, the second electrical conductor having a first end that extends out of the second channel at the rim of the dome-shaped outer surface; and
a second switch located at the second location of the dome-shaped outer surface, the second switch having a first state wherein an electrical connection between the second electrical conductor and the dome-shaped outer surface is broken and a second state wherein an electrical connection between the second electrical conductor and the dome-shaped outer surface is established.

5. The acetabular cup of claim 4, wherein:
(i) the first switch is configured such that the first switch is positioned in the second state when the first location of the dome-shaped outer surface contacts the patient's acetabulum, and
(ii) the second switch is configured such that the second switch is positioned in the second state when the second location of the dome-shaped outer surface contacts the patient's acetabulum.

6. The acetabular cup of claim 4 wherein:
(i) the first switch comprises a second end of the first electrical conductor, the second end of the first electrical conductor extending out of the first channel at the first location of the electrically conductive dome-shaped outer surface and positionable such that the second end of the first electrical conductor comes into contact with the electrically conductive dome-shaped outer surface when the first location of the dome-shaped outer surface contacts the patient's acetabulum, and (ii) the second switch comprises a second end of the second electrical conductor, the second end of the second electrical conductor extending out of the second channel at the second location of the electrically conductive dome-shaped outer surface and positionable such that the second end of the second electrical conductor comes into contact with the electrically conductive dome-shaped outer surface when the second location of the dome-shaped outer surface contacts the patient's acetabulum.

7. The acetabular cup of claim 1, wherein the electrically conductive dome-shaped outer surface includes:

(i) a first recessed area at the first location, the first switch being positioned in the first recessed area, (ii) a second recessed area at a second location of the dome-shaped outer surface, and (ii) a second channel defined in the dome-shaped outer surface, the second channel extending from the first recessed area to the second recessed area.

8. The acetabular cup of claim 7, further comprising:
a second switch positioned in the second recessed area, and
a second electrical conductor positioned in the second channel, the second electrical conductor electrically coupled to the first switch and the second switch.

9. The acetabular cup of claim 8, wherein the first switch comprises a first push-button switch and the second switch comprises a second push-button switch, each of the first and second push-button switches being biased to the first state.

10. The acetabular cup of claim 9, wherein the first switch is configured such that the first push-button switch is positioned in the second state when the first location of the dome-shaped outer surface contacts the patient's acetabulum and the second switch is configured such that the second push-button switch is positioned in the second state when the second location of the dome-shaped outer surface contacts the patient's acetabulum.

11. The acetabular cup of claim 8, further comprising a third electrical conductor electrically coupled to the second switch, a portion of the third electrical conductor being positioned in the first channel, the third electrical conductor having a first end that extends out of the first channel at the rim of the dome-shaped outer surface.

12. The acetabular cup of claim 1, wherein the first electrical conductor includes a non-conductive polymer cladding and a conductive polymer wire core located within the non-conductive polymer cladding.

13. An acetabular cup comprising:
an electrically conductive outer surface configured to confront a portion of a patient's acetabulum when the acetabular cup is implanted in the patient, the outer surface including a first channel defined therein that extends from a rim of the outer surface to a first location of the outer surface;
a first electrical conductor positioned in the first channel, the first electrical conductor having a first end that extends out of the first channel at the rim of the outer surface; and
a first push-button switch located at the first location of the outer surface, the first push-button switch having a first state wherein an electrical connection between the first electrical conductor and the outer surface is broken and a second state wherein an electrical connection between the first electrical conductor and the outer surface is established, and wherein the first push-button switch is biased to the first state.

14. The acetabular cup of claim 13, wherein the first push-button switch is configured such that the first push-button switch is positioned in the second state when the first location of the outer surface contacts the patient's acetabulum.

15. The acetabular cup of claim 13, wherein the electrically conductive outer surface includes a recessed area at the first location, the first push-button switch being positioned in the recessed area.

16. An orthopaedic prosthesis comprising:
a curved outer surface configured to confront a portion of a patient's bone when the orthopaedic prosthesis is implanted in the patient's bone, the curved outer surface being electrically conductive and having a channel defined therein, the channel extending from a rim of the curved outer surface to a first location of the curved outer surface, the first location is positioned near an apex of the curved outer surface; and
an electrical conductor positioned in the channel, the electrical conductor having a first end that extends out of the channel at the rim of the curved outer surface and a second end that extends out of the channel at the first location of the curved outer surface, the second end of the electrical conductor being positionable in a first position apart from the curved outer surface and a second position in contact with the curved outer surface.

17. The orthopaedic prosthesis of claim 16, wherein the second end of the electrical conductor is positioned such that the second end is moved to the second position when the first location of the curved outer surface contacts the patient's bone.

18. The orthopaedic prosthesis of claim 16, wherein the electrical conductor includes a non-conductive polymer cladding and a conductive polymer wire core located within the non-conductive polymer cladding.

19. The orthopaedic prosthesis of claim 18, wherein the conductive polymer wire core extends outwardly from the non-conductive polymer at the second end of the electrical conductor.

20. An acetabular cup comprising:
an dome-shaped outer surface configured to confront a portion of a patient's acetabulum when the acetabular cup is implanted in the patient, the dome-shaped outer surface including a channel defined therein that extends from a rim of the dome-shaped outer surface to a first location of the dome-shaped outer surface, the first location positioned near an apex of the dome-shaped outer surface;
a switch located at the first location of the dome-shaped outer surface;
a first electrical conductor positioned in the channel, the first electrical conductor having a first end that extends out of the channel at the rim of the dome-shaped outer surface and a second end electrically coupled to the switch;
a second electrical conductor positioned in the channel, the second electrical conductor having a first end that extends out of the channel at the rim of the dome-shaped outer surface and a second end electrically coupled to the switch,
wherein the switch has a first state wherein an electrical connection between the first electrical conductor and the second electrical conductor is broken and a second state wherein an electrical connection between the first electrical conductor and the second electrical conductor is established.

* * * * *